US00PP33939P2

(12) United States Plant Patent
Randag

(10) Patent No.: US PP33,939 P2
(45) Date of Patent: Feb. 1, 2022

(54) CALLA LILY PLANT NAMED 'DOZANWISL'

(50) Latin Name: *Zantedeschia sprengeri*
Varietal Denomination: Dozanwisl

(71) Applicant: Dümmen Group B.V., De Lier (NL)

(72) Inventor: Cecilius Jan-Jochem Randag, Koedijk (NL)

(73) Assignee: Dümmen Group B.V., De Lier (NL)

( * ) Notice: Subject to any disclaimer, the term of this patent is extended or adjusted under 35 U.S.C. 154(b) by 0 days.

(21) Appl. No.: 17/307,180

(22) Filed: May 4, 2021

(51) Int. Cl.
*A01H 5/02* (2018.01)
*A01H 6/10* (2018.01)

(52) U.S. Cl.
USPC ..... Plt./490

(58) Field of Classification Search
USPC ..... Plt./490
CPC ... A01H 5/02; A01H 5/00; A01H 6/10; A01H 6/56
See application file for complete search history.

*Primary Examiner* — June Hwu
(74) *Attorney, Agent, or Firm* — The Webb Law Firm

(57) ABSTRACT

'Dozanwisl' is a new variety of calla lily plant having pink colored spathes that produces 10-14 inflorescences per 14-16 cm tuber. The flower sterns are about 26-31 cm in height. The leaves are dark green with maculations present and a smooth texture.

2 Drawing Sheets

Botanical classification: *Zantedeschia sprengeri*.
Varietal denomination: 'Dozanwisl'.

BACKGROUND OF THE NEW PLANT

The present invention comprises a new and distinct variety of calla lily, botanically known as *Zantedeschia sprengeri* and hereinafter referred to by the varietal name 'Dozanwisl'. 'Dozanwisl' is a product of a planned breeding program, which had the objective of creating *Zantedeschia* hybrids for pot flower production in a wide range of colors with a classic flower shape. The new cultivar is a seedling selected from the crossing of *Zantedeschia sprengeri* seedling Z050967-865 (female parent, unpatented) with *Zantedeschia sprengeri* variety 'New York' (male parent, U.S. Plant Pat. No. 29,645). 'Dozanwisl' was selected in 2013 by the inventor in 't Zand, The Netherlands as one flowering plant within the progeny of the stated cross.

The first act of asexual reproduction of 'Dozanwisl' by tissue culture was performed by the inventor in November of 2013 in 't Zand, The Netherlands. Subsequent asexual reproductions by tissue culture at the same location have demonstrated that the combination of characteristics as herein disclosed for the new cultivar are retained and reproduced true to type through successive generations of asexual reproduction.

The following observations, measurements and comparisons describe plants at approximately 10 weeks from planting in 14 cm pots in 't Zand, The Netherlands under greenhouse conditions, which approximate those generally used in horticultural practice. Color references are made to The 2001 R.H.S. Colour Chart of The Royal Horticultural Society of London, $4^{th}$ Edition, except where general color terms of ordinary significance are used.

The present invention has not been evaluated under all possible environmental conditions. The phenotype may vary with variations in environment without a change in the genotype of the plant.

The following traits have been repeatedly observed and determined to be basic characteristics of 'Dozanwisl' which, in combination, distinguish this calla lily as a new and distinct cultivar:

1. Medium pink colored spathes with a dark throat spot;
2. Dark green colored leaves;
3. Few leaf maculations present; and
4. High inflorescence production.

The new variety is similar to its female parent in the following traits: spathe and stem color, throat spot presence, spathe and spadix length, and lanceolate leaf shape. However, 'Dozanwisl' exhibits a broader spathe width and weaker flower curve than its female parent. Further, its female parent does not have leaf maculations present. The new variety is similar to its male parent in the following traits: spathe and stem color, throat spot presence, spathe length, a weak flower curve, lanceolate leaf shape, and the presence of leaf maculations. However, 'Dozanwisl' exhibits a broader spathe width, later flowering time, shorter spadix length, and shorter plant height than its male parent.

Further, when compared to calla lily plant named 'Fangio' (U.S. Plant Pat. No. 28,196), both varieties exhibit numerous pink colored spathes, but the spathes of 'Dozanwisl' are medium pink in color, while the spathes of 'Fangio' are light pink and cream in color. Further, leaf maculations are exhibited by both varieties.

BRIEF DESCRIPTION OF THE DRAWINGS

The accompanying photographic drawings illustrate the new variety taken at approximately 10 weeks of age, with the colors being as nearly true as is possible with color illustrations of this type.

DESCRIPTION OF THE NEW PLANT

Figure 1:
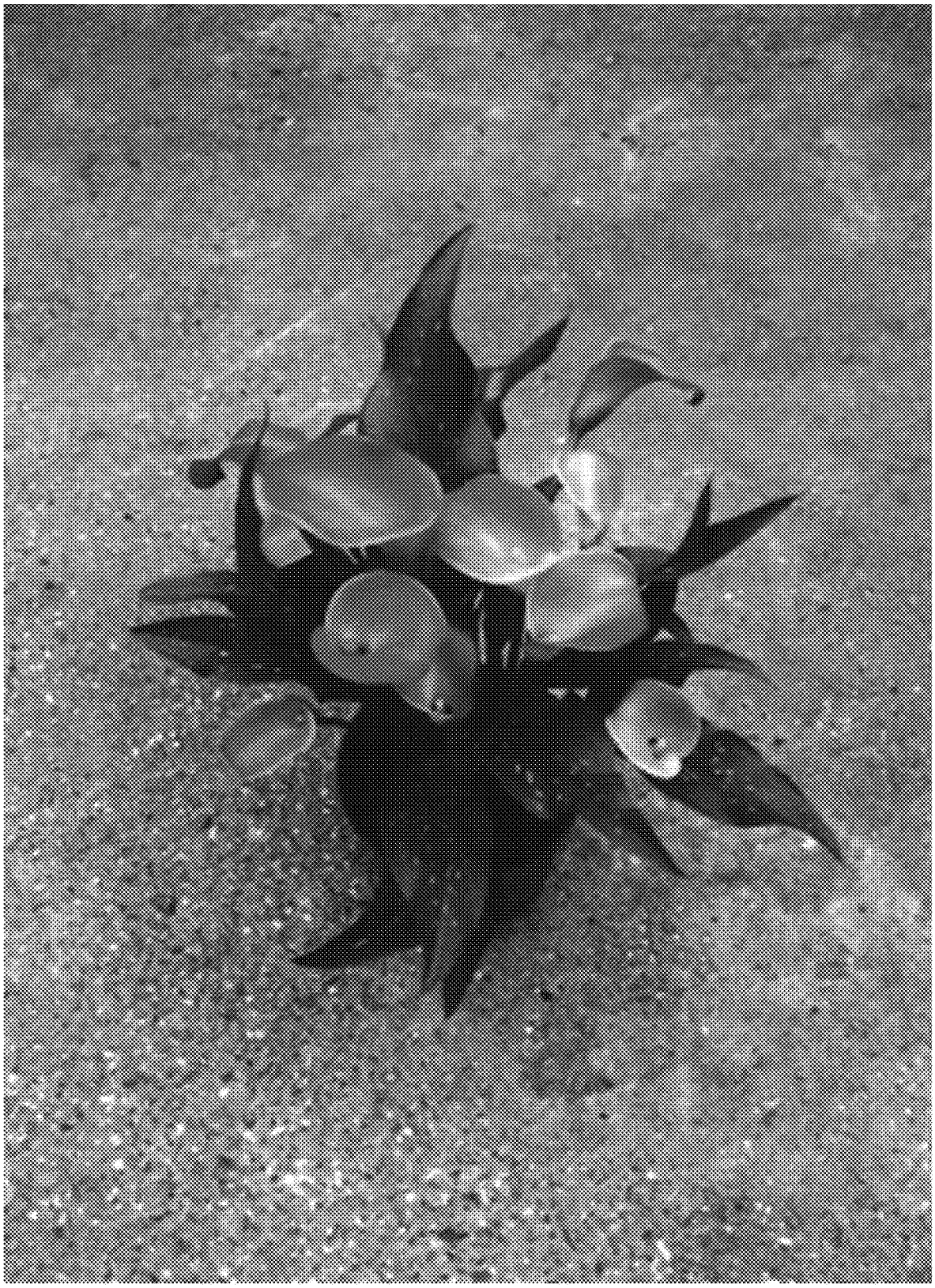
FIG. 1 illustrates a single flowering plant of the new variety.
Figure 2:
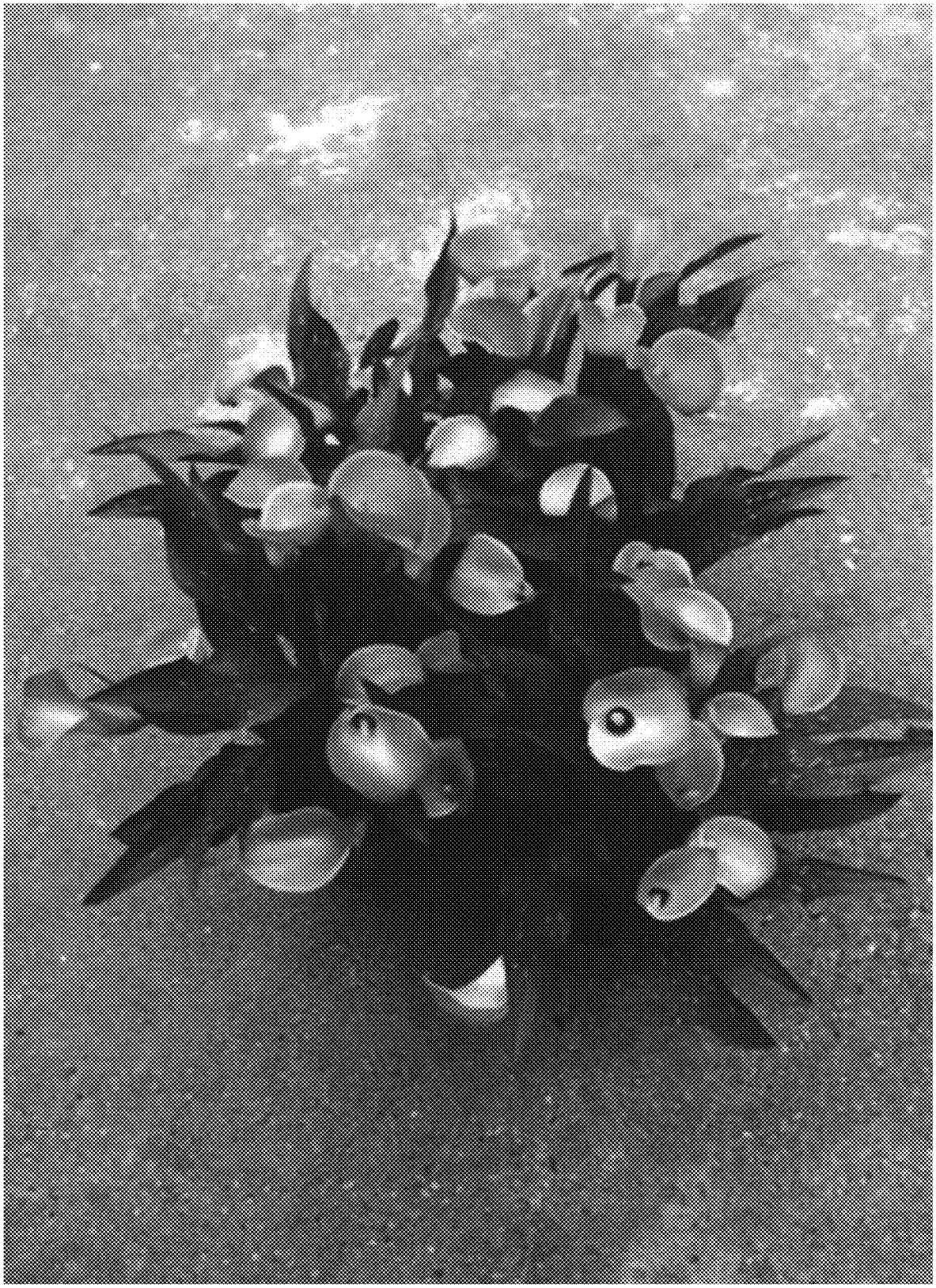
FIG. 2 illustrates multiple flowering plants of the new variety.

Type: Deciduous.
Size:
*Height of the leaf canopy above the soil.*—10-15 cm.
*Height of top of inflorescences above the soil.*—26-31 cm.
*Diameter.*—24-33 cm.
Form: Semi-spreading.
Number of inflorescences per tuber:
*Size 14-16 cm in diameter.*—10-14 inflorescences.
Branches:
*Number.*—Plentiful.
*Color.*—Yellow-Green Group RHS 144A to 144B.
*Young shoot color.*—Yellow-Green Group RHS 145A to 145C.
Leaves:
*Size.*—Width: 5-7.5 cm, with the broadest part being in the middle. Length: 17-19 cm.
*Number per plant.*—20-26.
*Leaf blade lobes.*—Absent.
*Shape.*—Lanceolate.
*Apex.*—Acuminate.
*Base.*—Attenuate.
*Margin.*—Entire; having a color of Green Group RHS 137C to 137D.
*Color.*—Upper surface: Generally, Green Group RHS 137A to 137B, with few, linear Greyed-White Group RHS 156C to 156D maculations present. Areas of Green Group RHS 137C, 137D, 138A, and 138B are randomly present throughout. Lower surface: Green Group RHS 138A to 138B, with few, linear Green-White Group RHS 157B to 157C maculations present.
*Veins.*—Configuration: Pinnate. Color: Yellow-Green Group RHS 147C to 147D.
*Surface texture.*—Smooth (both surfaces).
*Petiole.*—Length: 10-15 cm. Diameter: 10-14 mm. Color: The base is Yellow-Green Group RHS 146C to 146D, the upper part is Yellow-Green Group RHS 146D.
Roots:
*Color.*—White Group RHS 155C.
*Branching description.*—Fibrous root system. Several main roots emerge from the top of the tuber and form a small number of lateral roots.
Spathe:
*Size.*—Length (measured from opening to tip): 5-6 cm. Width: 4.5-6 cm. Height: 6-7 cm.
*Color (at all stages of maturity and fading).*—Throat spot: A large area of Greyed-Purple Group RHS N186B. Upper surface: Red-Purple Group RHS 73B to 73C. Lower surface: Red-Purple Group RHS 65A to 65B.
*Vein color.*—Yellow-Green Group RHS 150B to 150C.
*Shape.*—Funnel.
*Apex.*—Apiculate.
*Base.*—Attenuate.
*Margin.*—Entire with medium recurving and a color of White Group RHS 155A to 155B.
Spadix:
*Shape.*—Cylinder.
*Size.*—Length: 25-35 mm. Diameter: 6-9 mm.
*Color.*—Yellow-Orange Group RHS 15B to 15C.
*Position relative to spathe.*—Upright.
Peduncle:
*Size.*—Length: 18-25 cm. Diameter: 10-12 mm.
*Color.*—The upper part is Green Group RHS 143B to 143C, the lower part is Yellow-Green Group RHS 144B to 144C.
*Texture.*—Smooth.
Reproductive organs:
*Location of female organs.*—Basal position of the spadix.
*Location of male organs.*—Upper position of the spadix.
*Perianth.*—Conspicuous.
*Stamens.*—Presence: Not visible before pollen release. Number: Between 480 and 600. Pollen amount: Scarce. Color: Between White Group RHS 155B and 155C.
*Anther.*—Shape: Round. Length: Less than 1 mm. Color: Yellow Group RHS 8B to 8C.
*Filament.*—Length: Less than 1 mm. Color: White Group RHS 155D.
*Pistils.*—Number: 15 to 30. Length beyond perianth: About 1 mm.
*Stigma.*—Shape: Round. Size: Less than 1 mm.
*Style.*—Length: Less than 1 mm. Color: Green-White Group RHS 157B to 157C.
*Ovaries.*—Texture: Smooth. Length: Between 1 to 10 mm. Width: Between 1 to 10 mm. Color: The top color is Greyed-Red Group RHS 180C to 180D, the bottom color is Greyed-Orange Group RHS 164A to 164B.
Seeds:
*Length.*—2.8-4.1 mm.
*Width.*—2.3-2.9 mm.
*Color.*—Greyed-Green Group RHS 197B to 197C.
*Amount.*—12 per inflorescence.
Disease resistance: No unusual susceptibility/resistance to diseases noticed to date.
Pest resistance: No unusual susceptibility/resistance to pests noticed to date.
Heat tolerance: No heat tolerance.
Hardiness: Not tested to date.
Flowering: In general, the time from indoor and outdoor planting to first flowering takes about eight weeks in The Netherlands.
Lastingness: About two weeks on the plant.
Fragrance: None.

I claim:

1. A new and distinct variety of calla lily plant named 'Dozanwisl' as herein described and illustrated.

* * * * *